US005654298A

United States Patent [19]
Mills et al.

[11] Patent Number: 5,654,298
[45] Date of Patent: Aug. 5, 1997

[54] AMINE DERIVATIVES

[75] Inventors: Stuart Dennett Mills, Macclesfield; Rodney Brian Hargreaves, Poynton; Bernard Joseph McLoughlin, Macclesfield, all of England

[73] Assignee: Imperial Chemical Industries, London, England

[21] Appl. No.: 685,944

[22] Filed: Apr. 16, 1991

[30] Foreign Application Priority Data

Apr. 19, 1990 [GB] United Kingdom ............... 9008818

[51] Int. Cl.[6] .................. A01N 43/62; A01N 43/40; C07D 211/92; C07D 211/68
[52] U.S. Cl. ............ 514/221; 514/225.2; 514/227.8; 514/228.2; 514/229.8; 514/230.5; 514/233.2; 514/235.5; 514/298; 514/300; 514/312; 514/314; 514/318; 514/322; 514/334; 514/339; 514/340; 514/343; 514/354; 540/451; 540/461; 544/102; 544/105; 544/124; 544/122; 544/128; 544/129; 544/141; 544/142; 544/143; 546/109; 546/121; 546/122; 546/123; 546/153; 546/160; 546/193; 546/194; 546/257; 546/290; 546/299; 546/304; 546/347
[58] Field of Search ............... 546/347, 304, 546/297, 193, 160, 121, 122, 123, 153, 194, 257, 290; 544/35, 51, 60, 61, 102, 105, 129, 127, 128, 124, 141, 142, 143; 514/352, 334, 221, 225.2, 227.8, 228.2, 229.8, 230.5, 233.2, 235.5, 298, 300, 312, 314, 318, 322, 339, 346, 343; 540/451, 461

[56] References Cited

U.S. PATENT DOCUMENTS

| 2,748,124 | 5/1956 | Burtner ............... 260/256.4 |
| 2,845,425 | 7/1958 | Whitehead et al. ............ 260/256.4 |
| 4,067,874 | 1/1978 | Ursprung ............... 544/60 |
| 4,339,453 | 7/1982 | Grier et al. ............... 71/88 |
| 4,503,050 | 3/1985 | Wade ............... 514/222 |
| 4,725,600 | 2/1988 | Takaya et al. ............... 514/269 |
| 4,859,663 | 8/1989 | Greve et al. ............... 546/304 |
| 5,019,565 | 5/1991 | Baker et al. ............... 546/304 |

FOREIGN PATENT DOCUMENTS

| 0 090 733 | 10/1983 | European Pat. Off. . |
| 0 122 855 | 10/1984 | European Pat. Off. . |
| 0 139 613 | 5/1985 | European Pat. Off. . |
| 0 168 262 | 1/1986 | European Pat. Off. . |
| 199127 | 10/1986 | European Pat. Off. . |
| 243817 | 11/1987 | European Pat. Off. . |
| 0 322 133 | 6/1989 | European Pat. Off. . |
| 336494 | 10/1989 | European Pat. Off. . |
| 356412 | 2/1990 | European Pat. Off. . |
| 356413 | 2/1990 | European Pat. Off. . |

(List continued on next page.)

OTHER PUBLICATIONS

Archives of Biochemistry and Biophysics, vol. 280, No. 2, 1 Aug. 1990, pp. 274–283.
J. Het. Chem 9(4), 783–7. Aug. 1972.

J. Am. Chem. Soc. 105, 1983, 5661–5664.

J. Am. Chem. Soc., 103, 1981, 6148–6151.

Y.G. Kagaku"Preparation of 1–Phenyl–Polyhydro–s–Triazines" *Org. Syn. Chem.*, 34(6), 417–424, (1976); English Translation (Chemical Abstracts, vol. 86, No. 9, Abstr. No. 55393M).

(List continued on next page.)

*Primary Examiner*—C. Warren Ivy
*Assistant Examiner*—Raymond Covington
*Attorney, Agent, or Firm*—Cushman, Darby & Cushman

[57] ABSTRACT

This invention concerns novel aminopyridinium compounds of the formula I wherein $R^1$, $R^2$, $R^3$, $R^5$ and $R^6$ are selected from the following combinations:

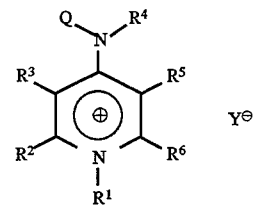

(a) one of $R^2$ and $R^6$ is a basic group selected from amino, alkylamino, dialkylamino of up to eight carbon atoms, pyrrolidino, piperidino and morpholino, or is alkyl, alkenyl, alkoxyalkyl, alkoxy, alkylthio, phenyl, phenylalkyl, cycloalkyl or cycloalkylalkyl; and the other of $R^2$ and $R^6$ is hydrogen, alkyl or one of the above defined basic groups;

$R^1$ is alkyl, alkenyl, cycloalkyl, phenyl, phenylalkyl, cycloalkylalkyl; and $R^3$ and $R^5$ are independently hydrogen, alkyl or alkenyl;

(b) $R^2$ is a basic group as defined above, $R^5$ and $R^6$ together form alkylene or, together with the appendant carbon atoms of the pyridine ring, complete a benzene ring; has any of the meanings defined in (a) above; and $R^3$ is hydrogen, alkyl or alkenyl; and (c) R2 has any of the meanings defined above and $R^6$ is a group of the formula —$NR^7$.A— in which A together with $R^1$ forms an ethylene, trimethylene or tetramethylene link and $R^7$ is hydrogen or alkyl; and $R^3$ and $R^5$ have, independently, any of the meanings defined in (a) above; and wherein $R^4$ is hydrogen, cycloalkylalkyl, alkyl, alkenyl, alkynyl or phenylalkyl; and Q is phenyl; or the group Q.N($R^4$)— together constitutes an azaheterocyclic moietyo; Y is a physiologically acceptable anion; and any one or more of said phenyl or benzene moieties may optionally be unsubstituted or bear one or more selected substituents.

The invention also includes certain closely related anhydrobase derivatives which, like the formula I compounds, possess beneficial effects on the cardiovascular system. Also included are pharmaceutical compositions and processes for the manufacture of the various novel compounds.

13 Claims, No Drawings

FOREIGN PATENT DOCUMENTS

| | | |
|---|---|---|
| 2233060 | 1/1975 | France . |
| 1 241 832 | 6/1967 | Germany . |
| 3703633 | 8/1987 | Germany . |
| 3639563 | 6/1988 | Germany . |
| 37 17480 | 12/1988 | Germany . |
| 0 658 205 | 10/1951 | United Kingdom . |
| 814947 | 6/1959 | United Kingdom . |
| 0 815 833 | 7/1959 | United Kingdom . |
| 1 020 306 | 2/1966 | United Kingdom . |
| 1132306 | 10/1968 | United Kingdom . |
| 1 229 413 | 4/1971 | United Kingdom . |
| 1 502 912 | 3/1978 | United Kingdom . |
| 2071092 | 9/1981 | United Kingdom . |
| WO87/01706 | 3/1987 | WIPO . |

OTHER PUBLICATIONS

Chemical Abstracts, vol. 80, No. 1, Abstr. No. 3472T, Jan. 7, 1974.

Chemical Abstracts, vol. 80, No. 1, Abstr. No. 3471S, Jan. 7, 1974.

Chemical Abstracts, vol. 58, No. 2, No. 1451e, Jan. 21, 1963.

Chemical Abstracts, vol. 111, No. 17, No., 153834K, Oct. 23, 1989.

Chemical Abstracts, vol. 79, No. 17, No. 105194a, Oct. 29, 1973.

Chemical Abstracts, vol. 105, No. 15, No. 133849s, Oct. 13, 1986.

Chemical Abstracts, vol. 106, No. 17, No. 138408c, Apr. 27, 1987.

Chemical Abstracts, vol. 69, No. 17, No. 67335f, Oct. 21, 1968.

Chemical Abstracts, vol. 86, No. 23, No. 171370u, Jun. 6, 1977.

Chemical Abstracts, vol. 108, No. 3, No. 21816j, Jan. 18, 1988.

W.A. Denny et al. "Potential Antitumor Agents. 29. Quantitative Structure–Activity Relationships for the Antileukemic Bisquaternary Ammonium Heterocycles" *J. Med. Chem.*, 22(2), 134–50 (1979).

G.J. Atwell et al. "Potential Antitumor Agents. VIII. Bisquaternary Salts" *J. Med. Chem.*, 11, 690–4 (1968).

AMINE DERIVATIVES

This invention concerns novel aminoheterocyclic compounds and, more particularly, novel aminopyridinium derivatives, which possess beneficial effects on the cardiovascular system (and in particular beneficial effects modulated via the sino-atrial node), pharmaceutical compositions containing such a derivative as active ingredient, and processes for the manufacture of and medical use of the said derivatives.

Although numerous compounds are known to have medically useful effects on the cardiovascular system, hitherto there have not existed satisfactory agents which modulate the action of the sino-atrial node in warm-blooded animals such as man in a beneficial, selective and medically useful manner so that the agents are useful in treating cardiovascular disorders associated with an inappropriately elevated heart rate and yet have minimal effects on other haemodynamic parameters such as blood pressure or cardiac output. It is an object of the invention to provide such an agent which has, inter alia, bradycardic properties.

Certain quaternary pyridinium salts which bear a phenyl substituent at the 2- and 6-position and an amino group at the 4-position have been reported (J. Am. Chem. Soc., 105[17], 5661–4; J. Am. Chem. Soc., 103[20], 6148–51; and J. Heterocyclic Chem., 9[4], 783–7). The rate parameters and base catalysis of these compounds was investigated.

According to the invention there is provided an aminopyridine derivative of the formula I (set out hereinafter, together with the other chemical formulae appearing herein in Roman numerals) wherein $R^1$, $R^2$, $R^3$, $R^5$ and $R^6$ are selected from the following combinations:

(a) one of $R^2$ and $R^6$ is a basic group selected from amino, (1–6C)alkylamino, dialkylamino of up to eight carbon atoms, pyrrolidino, piperidino and morpholino, or is (1–6C)alkyl, (3–6C)alkenyl, (1–4C)alkoxy(1–4C) alkyl, (1–6C)alkoxy, (1–6C)alkylthio, phenyl, phenyl (1–4C)alkyl, (3–6C)cycloalkyl or (3–6C)cycloalkyl (1–4C)alkyl; and the other of $R^2$ and $R^6$ is hydrogen, (1–6C)alkyl or one of the above defined basic groups; $R^1$ is (1–8C)alkyl, (3–6C)alkenyl, (4–7C)cycloalkyl, phenyl, phenyl(1–4C)alkyl, (3–6C)cycloalkyl-(1–4C) alkyl; and $R^3$ and $R^5$ are independently hydrogen, (1–4C)alkyl or (3–6C)alkenyl;

(b) $R^2$ is a basic group as defined above, $R^5$ and $R^6$ together form (3–6C)alkylene or, together with the appendant carbon atoms of the pyridine ring, complete a benzene ring; $R^1$ has any of the meanings defined in (a) above; and $R^3$ is hydrogen, (1–4C)alkyl or (3–6C) alkenyl; and (c) R2 has any of the meanings defined above and $R^6$ is a group of the formula —$NR^7$.A— in which A together with $R^1$ forms an ethylene, trimethylene or tetramethylene link and $R^7$ is hydrogen or (1–6C)alkyl; and $R^3$ and $R^5$ have, independently, any of the meanings defined in (a) above;

and wherein $R^4$ is hydrogen, (3–6C)cycloalkyl-(1–4C)alkyl, (1–6C)alkyl, (3–6C)alkenyl, (3–6C)alkynyl or phenyl (1–4C)alkyl; and Q is phenyl; or the group Q.N($R^4$)— together constitutes an azaheterocyclic moiety selected from pyrrolidine, pyrrole, piperidine, didehydropiperidine, morpholine, thiomorpholine and hexamethyleneimine, which azaheterocyclic moiety may itself optionally bear an (1–4C)alkyl, phenyl or phenyl(1–4C)alkyl substituent, or one or two benzene moieties fused thereto; Y is a physiologically acceptable anion; and any one or more of said phenyl or benzene moieties may optionally be unsubstituted or bear one or more substituents independently selected from halogeno, (1–4C)alkyl, (3–6C)alkenyl, (1–4C)alkoxy, cyano, trifluoromethyl, nitro, amino, hydroxy, (1–4C) alkylamino, dialkylamino of up to six carbon atoms, (1–4C) alkylthio, (1–4C)alkylsulphinyl, (1–4C)alkylsulphonyl and (1–4C)alkylenedioxy.

It will be understood that when $R^4$ is hydrogen, or when $R^2$ or $R^6$ is amino or alkylamino, or when $R^6$ is a group of the formula —$NR^7$.A— in which $R^7$ is hydrogen, the amine derivatives of the invention may exist in another tautomeric form to that depicted in formula I, or in a mixture of one or more of the possible tautomeric forms. It will also be understood that when one of the substituents in the formula I compounds contains a chiral centre, the compounds of the invention may exist in, and be isolated in, optically active or racemic form. The invention includes any tautomeric, optically active or racemic from of a compound of formula I which possesses the afore-mentioned beneficial pharmacological effects.

The compounds of formula I are quaternary salts and in some cases, for example, when $R^2$ or $R^6$ is alkylamino or when $R^6$ is a group of the formula —$NR^7$.A— in which $R^7$ is hydrogen, may be converted, for example by treatment with a quaternary ammonium hydroxide (and especially one in macroreticular resin form) to the corresponding non-ionic anhydro-base forms of the formula Ia, Ib or Ic, respectively, (or to a tautomeric form thereof when $R^4$ is hydrogen or when the other of the groups $R^2$ and $R^6$ is amino or alkylamino). Such non-ionic forms of the formula Ia, Ib or Ic in which alk stands for (1–4C)alkyl and n is the integer 2,3 or 4 are provided as a further feature of the invention and may readily be reconverted to the quaternary salt form, for example, by treatment with the appropriate acid of the formula H.Y.

A particular value for $R^1$ when it is alkyl is, for example, (1–6C)alkyl, such as methyl, ethyl, propyl, butyl or pentyl, of which values methyl and ethyl are generally preferred.

A particular value for $R^1$, $R^2$, $R^3$, $R^4$, $R^5$ or $R^6$ when it is alkenyl is, for example, allyl, but-2-enyl or 2-methyl-2-propenyl.

A particular value for $R^1$ when it is cycloalkyl is, for example, cyclopropyl, cyclobutyl, cyclopentyl, cyclohexyl or cycloheptyl, and for $R^2$ or $R^6$ is, for example, cyclopropyl, cyclobutyl, cyclopentyl or cyclohexyl.

A particular value for $R^1$, $R^2$, $R^4$ or $R^6$ when it is phenyl(1–4C)alkyl or for a phenyl(1–4C)alkyl substituent on an azaheterocyclic moiety is, for example, benzyl, 1-phenylethyl or 2-phenylethyl, any of which may optionally bear a substituent as defined above.

A particular value for $R^1$, $R^2$, $R^4$ or $R^6$ when it is cycloalkyl-alkyl is, for example, cyclopropyl-methyl, cylopentyl-methyl, cyclohexylmethyl or 2-(cyclohexyl) ethyl.

A particular value for $R^2$, $R^3$, $R^5$, $R^6$ or $R^7$ when it is alkyl, or for an alkyl substituent on an azaheterocyclic moiety, is, for example, methyl, ethyl, isopropyl or butyl.

A particular value for $R^2$ or $R^6$ when it is alkoxy is, for example, methoxy, ethoxy or propoxy, when it is alkylthio is, for example, methylthio or ethylthio, and when it is alkoxyalkyl is for example, methoxymethyl, 2-methoxyethyl or 2-ethoxyethyl.

A particular value for $R^5$ and $R^6$ when together they form (3–6C)alkylene is, for example, trimethylene, tetramethylene, pentamethylene or a group of the formula —$CH_2$.C($CH_3$)$_2$.$CH_2$— or —$CH_2$.C($CH_3$)$_2$.$CH_2$.$CH_2$—.

A particular value for $R^4$ when it is alkyl is, for example, methyl, ethyl, propyl, isopropyl, butyl, isobutyl, sec-butyl or pentyl.

A particular value for $R^4$ when it is alkynyl is, for example, prop-2-ynyl or but-2-ynyl.

A particular value for $R^2$ or $R^6$ when it is alkylamino is, for example, methylamino, ethylamino, propylamino or butylamino, and when it is dialkylamino is, for example, dimethylamino, diethylamino, methylpropylamino or dipropylamino.

Particular values for optional substituents which may be present as defined hereinabove on a phenyl or benzene moiety include, by way of example:

for halogeno, fluoro, chloro and bromo;

for alkyl, methyl, ethyl and propyl;

for alkenyl, allyl and 2-methyl-2-propenyl;

for alkoxy, methoxy, ethoxy and propoxy;

for alkylamino, methylamino and ethylamino;

for dialkylamino, dimethylamino and diethylamino;

for alkylthio, methylthio and ethylthio;

for alkylsulphinyl, methylsulphinyl and ethylsulphinyl;

for alkylsulphonyl, methylsulphonyl and ethylsulphonyl; and for alkylenedioxy, methylenedioxy and isopropylidenedioxy.

In general, it is preferred that, when Q is phenyl it is unsubstituted or bears up to three substituents.

Specific values for Q include, for example, phenyl, 4-chlorophenyl, 4-methylphenyl, 2nitrophenyl, 2-methoxyphenyl, 4-methylthiophenyl, 2,5-dinitrophenyl, 3,5-dimethylphenyl and 3,5-dichlorophenyl.

Specific values for the group $Q.N(R^4)$— when it constitutes an azaheterocyclic moiety, include, for example, pyrrolidino, piperidino, morpholino, thiomorpholino, benzomopholino, 4-phenylpiperidino, hexamethyleneimino, 1,2,4,5-tetrahydro-1-pyridyl, 1,2,3,4-tetrahydro-1-quinolyl, 1,2,3,4-tetrahydro-2-isoquinolyl, 1-indolyl, 1-indolinyl, 3-methyl-1-indolinyl, 3-methyl-1-indolyl, 3-ethyl-1-indolyl, 3-ethyl-1-indolinyl, 3-propyl-1-indolyl, 5-bromo-1-indolyl, 9-carbazolyl, 10-phenothiazinyl and 10-phenoxazinyl.

A preferred value for $R^1$ is, for example, methyl, ethyl, butyl, phenyl or cyclohexyl, for $R^2$ is, for example, methyl or ethyl, and for R6 is, for example, methyl, ethyl, amino, methylamino or ethylamino.

A preferred values for $R^4$ when Q is phenyl (unsubstituted or substituted as defined above) is, for example, (1–6C)alkyl (especially ethyl), (3–6C)alkenyl, (3–6C)alkynyl (especially butynyl) or phenyl(1–4C)alkyl. A particularly preferred value for $R^4$ is ethyl.

A preferred value for $R^4$ when the group $Q.N(R^4)$— constitutes an azaheterocyclic moiety includes, for example an ethylene or vinylene group which completes an indoline or indole ring, respectively, including two adjacent carbon atoms of the benzene ring Q and the nitrogen atom of the group —$N(R^4)$—.

A group of compounds of the invention which is of interest comprises those compounds of the formula II wherein:

Ra is (1–6C)alkyl, phenyl, phenyl(1–4C)alkyl or (3–6C) cycloalkyl; Rb is hydrogen, (1–6C)alkyl, phenyl, phenyl(1–4C)alkyl, (3–6C)cycloalkyl or (3–6C) cycloalkyl-(1–4C)alkyl, amino, (1–4C)alkylamino or dialkylamino of up to 6 carbon atoms; Rc is hydrogen, (3–6C)cycloalkyl-(1–4C)alkyl, (1–6C)alkyl, (3–6C) alkenyl, (3–6C)alkynyl or phenyl(1–4C)alkyl;
and Qa is phenyl;

or the group Qa.N(Rc)— together constitutes an azaheterocyclic moiety selected from pyrrolidine, pyrrole, piperidine, didehydropiperidine, morpholine and hexamethyleneimine, which azaheterocyclic moiety may itself optionally bear a methyl, ethyl, phenyl or benzyl substituent, or may have one or two benzene moieties fused thereto;

Rd is hydrogen or methyl; Re and Rf are independently selected from hydrogen and (1–4C)alkyl, or together form (3–6C)alkylene; Y is a physiologically acceptable anion; and wherein any one or more of said phenyl or benzene moieties may optionally be unsubstituted or bear one or more substituents independently selected from halogeno, trifluoromethyl, cyano, nitro, (1–4C) alkyl and (1–4C)alkoxy.

A further group of compounds of the invention of interest comprises those compounds of formula III wherein Ra, Rb, Rc, Rd, Qa and Y have the meanings defined above for formula II, and Rg is hydrogen or (1–4C)alkyl.

Specific values for Ra, Rb, Rc, Rd and Qa include, for example, the relevant values mentioned hereinabove for $R^1$, $R^2$, $R^4$, $R^5$ and Q. A particular value for Re, Rf or Rg when it is alkyl is, for example, methyl or ethyl and for Re and Rf when together they form alkylene is, for example, tetramethylene or pentamethylene.

A preferred value for Ra is, for example, methyl, ethyl, butyl, phenyl or cyclohexyl, for Rb is, for example, methyl, ethyl, amino, methylamino or ethylamino and for Rd is, for example, hydrogen.

Thus a group of compounds of interest include those of the formula I wherein:

$R^1$ is (1–6C)alkyl, phenyl, phenyl(1–4C)alkyl or (3–6C) cycloalkyl; $R^2$ is hydrogen, (1–6C)alkyl, phenyl, phenyl(1–4C)alkyl, (3–6C)cycloalkyl or (3–6C) cycloalkyl-(1–4C)alkyl, amino, (1–4C)alkylamino or dialkylamino of up to 6 carbon atoms; $R^4$ is hydrogen, (3–6C)cycloalkyl-(1–4C)alkyl, (1–6C)alkyl, (3–6C) alkenyl, (3–6C)alkynyl or phenyl(1–4C)alkyl;
and Q is phenyl;

or the group $Q.N(R^4)$— together constitutes an azaheterocyclic moiety selected from pyrrolidine, pyrrole, piperidine, didehydropiperidine, morpholine and hexamethyleneimine, which azaheterocyclic moiety may itself optionally bear a methyl, ethyl, phenyl or benzyl substituent, or may have one or two benzene moieties fused thereto;

$R^5$ is hydrogen or methyl; $R^3$ is hydrogen; R6 is a group of formula IIa in which Re and Rf are independently selected from hydrogen and (1–4C)alkyl, or together form (3–6C)alkylene; Y is a physiologically acceptable anion; and wherein any one or more of said phenyl or benzene moieties may optionally be unsubstituted or bear one or more substituents independently selected from halogeno, trifluoromethyl, cyano, nitro, (1–4C) alkyl and (1–4C)alkoxy.

A further group of compounds of interest include those of formula I wherein $R^1$, $R^2$, $R^3$, $R^5$, $R^4$ and Q are as defined above, and R6 is hydrogen or (1–4C)alkyl.

Particular, specific and preferred values for $R^1$, $R^2$, $R^3$, $R^5$, $R^4$, $R^6$, Re, Rf and Q are as defined above.

It is particularly preferred, for example, that Q is phenyl; $R^1$ is methyl, ethyl, butyl, phenyl or cyclohexyl; $R^2$ is methyl or ethyl; $R^5$ is hydrogen; $R^3$ is hydrogen; $R^4$ is ethyl or $R^4$ is ethylene or vinylene completing an indoline or indole ring, respectively, including two adjacent carbon atoms of the benzene ring Q and the nitrogen atom of the group —$N(R^4)$—; $R^6$ is methyl or ethyl; Y is a physiologically acceptable anion; and wherein the phenyl ring Q may optionally be unsubstituted or bear one or two substituents independently selected from fluoro, chloro, bromo, methyl, and methoxy.

A further group of compounds of the invention and which is of special interest comprises compounds of the formula IV wherein Qb is phenyl; Rh is (1–4C)alkyl (such as methyl or ethyl); Ri is (1–4C)alkyl (such as methyl or ethyl), amino, (1–4C)alkylamino (such as methylamino or ethylamino) or dialkylamino of up to 6 carbon atoms (such as dimethylamino); Rj is hydrogen, (1–6C)alkyl (such as methyl, ethyl, propyl or pentyl) or (3–6C)alkenyl (such as allyl); or the group Qb.N(Rj)— together constitutes an azaheterocyclic moiety selected from pyrrolidine, piperidine, morpholine, which azaheterocyclic moiety may itself optionally bear a methyl, ethyl, phenyl or benzyl substituent, or may have one or two benzene moieties fused thereto; and Rk is hydrogen or (1–4C)alkyl (such as methyl or ethyl); Y is a physiologically acceptable anion; and wherein a phenyl or benzene moiety as defined above, may optionally be unsubstituted or bear one or two substituents independently selected from halogeno (such as fluoro, chloro or bromo), (1–4C)alkyl (such as methyl) and (1–4C)alkoxy (such as methoxy).

Particular physiologically acceptable counter anions Y include, for example, halide (such as chloride, bromide or iodide), sulphate, fluoroborate, phosphate, nitrate, acetate, benzoate, butyrate, citrate, tartrate, dibenzoyltartrate, fumarate, trifluoroacetate, methosulphate and p-toluenesulphonate.

Particular groups of non-ionic anhydro-bases of the invention defined above comprise compounds of the formula Ia, Ib or Ic in which $R^1$, $R^2$, $R^3$, $R^4$, $R^5$, $R^6$ and Q have any of the meanings defined above, alk stands for (1–4C)alkyl (especially methyl or ethyl), and n is the integer 2, 3 or 4.

Compounds of the invention which are of particular interest include the compounds described in the accompanying Examples of which, the compounds described in Examples 1,6,7,8,9,10,13,14 and 15 are of special interest. The latter compounds in the form described herein (or in the form of an alternative physiologically acceptable counter anion), are provided as a further feature of the invention.

The compounds of the invention may be obtained by standard procedures of organic chemistry already known to be applicable to the preparation of structurally analogous compounds, for example those procedures described in standard reference works on the chemistry of the pyridines. Such procedures for the manufacture of the novel compounds of formula I are provided as a further feature of the invention and are illustrated by the following preferred processes in which the various generic radicals have any of the meanings defined hereinbefore.

a) An amino compound of the formula V is reacted with an alkylating agent of the formula $R^1.Z$, in which Z is a suitable leaving group.

A preferred value of Z is, for example, halide (especially iodide, bromide or chloride), sulphate, methosulphate and p-toluenesulphate.

The reaction is generally carried out by heating the alkylating agent with the compound of formula V at a temperature of, for example, 40°–120° C. and is conveniently carried out in a suitable solvent or diluent, for example, in an ether such as dioxane, tetrahydrofuran or t-butyl methyl ether.

The starting materials of formula V can be made, for example, by reaction of the corresponding halogeno pyridine of the formula VI wherein X is chloro or bromo with the appropriate amine of the formula Q.N($R^4$)H at a temperature in the range, for example, 40°–150° C. This particular reaction may be carried out in the presence of a suitable solvent or diluent such as a (1–4C)alkanol or N,N-dimethylformamide, or as a melt of the reagents alone. The amines of the formula Q.N($R^4$)H and the compounds of formula VI are in general known or may be made by conventional techniques well known in the art of organic and pyridine chemistry.

b) A pyridinium salt of the formula VII wherein X is a suitable leaving group and Y has the meanings defined above, is reacted with an amine of the formula Q.N($R^4$)H.

The process will be seen to be analogous to that described above for the production of the starting materials of the formula VI and analogous conditions may in general be used. Thus, the process is generally carried out at an elevated temperature in the range, for example, 20°–15°° C. and in the presence of a suitable solvent or diluent such as a (1–4C)alkanol or N,N-dimethylformamide.

A particularly suitable leaving group X is, for example, halogeno (especially chloro or bromo), dichlorophosphinoyl [—O.PO.Cl$_2$], or dibromophosphinoyl [—O.PO.Br$_2$]. The latter two groups may conveniently be introduced in situ by the reaction of the corresponding pyridone of formula VIII with phosphorus oxychloride or oxybromide, respectively, for example as described in the accompanying Examples. [Note: it will be appreciated by those skilled in the art that the precise identity of the group X is not generally critical to the process (b)].

The pyridinium salts of formula VII may alternatively be obtained, for example, by analogy with process (a) above, that is by reaction of a halogeno pyridine of the formula VI with the appropriate alkylating agent of the formula $R^1.Y$ and, in particular, with an iodide or bromide of the formula $R^1.I$ or $R^1.Br$. Alternatively, they may also be obtained, for example, by reaction of the appropriate pyridinone of formula VIII with a suitable chlorinating agent such as phosphorus oxychloride, for example as illustrated in the accompanying Examples. The pyridinones of formula VIII may themselves be obtained by standard procedures.

c) For those compounds wherein $R^6$ is amino, alkylamino, dialkylamino, pyrrolidino, piperidino or morpholino as defined above, a pyridinium salt of the formula IX wherein X is a suitable leaving group is reacted with the appropriate amine selected from ammonia, (1–6C) alkylamine, dialkylamine of up to 6 carbon atoms, pyrrolidine, piperidine and morpholine, or a salt thereof with a (1–4C)alkanoic acid (such as acetic acid).

The process will be seen to be analogous to process (b) described above and analogous considerations and reaction conditions may in general be used. In general an excess of the starting amine or an alkanoic acid salt thereof will be used. The starting compounds of formula IX may be obtained in a generally similar manner to those for the formula VII compounds.

It will be appreciated that she counter anion Y$^-$ in the formula I compounds may readily be changed, for example, by reaction of the formula I compound with a suitable salt such as a silver salt or by ion-exchange chromatography on a column of a basic macroreticular resin in the form of its salt with the desired counter anion, or another conventional method. When the non-ionic anhydro-base form of a compound of I is required, (for example a compound of formula Ia, Ib or Ic), it may be obtained, for example, by reaction of the appropriate compound of formula I with a strong base such as a quaternary ammonium hydroxide, particularly a macroreticular resin containing quaternary ammonium hydroxide groups. The process is conveniently carried out by exposing a solution of the compound of formula I in an aqueous solvent such as an aqueous (1–4C)alkanol (for example methanol, ethanol or 2-propanol) to the resin at or near ambient temperature, for example by trickling the solution over a bed or through a column of the resin. The anhydo-base form may then conveniently be returned to an ionic form of formula by reaction with the appropriate acid of formula H.Y.

It will also be appreciated that certain of the various optional substituents in the compounds of the invention may be introduced by standard aromatic substitution reactions or generated by conventional functional group modifications either prior to or immediately following process (a) or (b) above. Such reactions and modifications include, for example, introduction of nitro or halogeno, reduction of a nitro, reductive alkylation of nitro, oxidation of alkylthio to alkylsulphinyl or alkylsulphonyl and reduction of alkynyl or alkenyl. The reagents and reaction conditions for such procedures are well known in the chemical art.

Many of the intermediates used in the preparation of the compounds of the present invention are novel are thus provided as a further feature of the present invention. In particular there is provided a compound of formula V in which $R^2$, $R^3$, $R^4$, $R^5$, $R^6$ and Q may take any of the values stated above; a compound of formula VII in which $R^1$, $R^2$, $R^3$, $R^5$, $R^6$, Y and X may take any of the values stated above; and a compound of formula IX in which $R^1$, $R^2$, $R^3$, $R^4$, $R^5$, $R^6$, X, Y and Q may take any of the values stated above;

As indicated above, the compounds of the invention possess useful pharmacological properties and modulate the action of the sino-atrial node in warm-blooded animals in a beneficial, selective and medically useful manner so that the agents are useful in treating cardiovascular disorders associated with an inappropriately elevated heart rate and with minimal effects on other haemodynamic parameters such as blood pressure or cardiac output. The beneficial and selective effects of the cardiovascular system may be demonstrated using the following standard laboratory techniques.

a) Bradycardic effect (reduction in beating rate of the spontaneously beating isolated guinea pig right atrium).

This technique involves the dissection of the right atrium from a guinea pig heart, taking care not to damage the sino-atrial node region. The atrium is established in oxygenated (95% $O_2$; 5% $CO_2$) Tyrode's solution [containing 8.0 g NaCl, 0.19 g KCl, 0.025 g $MgCl_2$, 0.05 g $NaH_2PO_4$, 1.0 g $NaHCO_3$, 0.2 g $CaCl_2$ and 2.7 g glucose, per liter of deionised water] between two platinum spikes which are connected via an amplifier to a conventional rate-meter, triggered by the action potentials across the atrium. The preparation is bathed in oxygenated Tyrode's solution at 37 degrees Celsius and allowed to equilibrate for 30 minutes before the addition of a solution of the test compound in a mixture of dimethyl sulphoxide and Cremophor EL, diluted as required with Tyrode's solution. Further solutions of test compound are then added cumulatively at 15 minute intervals or when a steady-state beating rate has been attained. This enables an $IC_{20}$ (i.e. the micromolar concentration required to reduce the beating rate by 20%) to be calculated. Typically, a compound of formula I will have an $IC_{20}$ of 10 micromolar or less.

b) Effect on contractile force of electrically stimulated isolated guinea pig left atrium.

This technique involves the dissection of the left atrium from a guinea pig heart into oxygenated Tyrodes solution. The atrium is then clamped in an polyacrylate plastic holder containing two stainless steel-stimulating electrodes. The free end of the atrium (normally the atrial appendage) is attached with silk thread to an isometric force transducer. The atrium is then set under a resting tension of 1 g and is allowed to equilibrate in oxygenated Tyrode's solution for 20 minutes before being stimulated into beating by application of 2.5 Hz, 3 mS pulses at 1.5 times the threshold voltage (normally in the range 3–7 V). A solution ($10^{-5}$M or less) of the test compound [made up as in (a) above] is then added and the effect on contractile force measured. In this way a comparison of the effect with that of a control solution without any test compound can be obtained. Typically, at a concentration in the range 1–30 micromolar compounds of the formula I show <15% reduction in contractile force.

c) Bradycardic effect in the anaesthetised rat

This technique involves the use of Wistar rats (Alderley Park strain) which are pre-anaesthetised by intravenous injection of alphaxalone/alphadalone (1.5 ml per kg). A polyethylene cannula is inserted into the jugular vein and anaesthesia is maintained by infusion of alphaxalone/alphadalone at a rate of 0.025–0.12 ml per kg per minute. A polyethylene cannula is also inserted into the carotid artery and connected to a pressure transducer filled with physiological saline solution. The arterial blood pressure signal is used to trigger an internally calibrated heart rate meter and the transducer is calibrated with a mercury manometer. The output of the heart rate meter and of the pressure transducer are then recorded simultaneously on a standard chart recorder. After cannulation, the rat preparation is allowed to stabilise for 10 minutes. A solution of a test compound [made up as in (a) above, in a volume of 1 ml per kg] is then administered via the venous cannula in four cumulative doses separated by 5 minute intervals. A group of five rats is used for each test compound. The effects on heart rate and blood pressure may then be determined in comparison with those of a control injection. Typically, a compound of formula I active using this procedure will require an i.v. dose of 5 mg/kg or less to produce a 30% reduction in heart rate (i.e. the $ED_{30}$ dose).

The beneficial effects of a test compound on the cardiovascular system, such as bradycardic effects without an adverse effect on heart force, blood pressure and or cardiac output, may also be determined in anaesthetised dogs and in dogs in which tachycardia has been induced by exercise. In general, the compounds of the invention show significant and predominantly selective bradycardic effects as evidenced by activity in at least two of the above mentioned test techniques. No overt toxicity is generally observed with the compounds of formula I in the above in vivo test techniques at doses several multiples of those at which significant bradycardic effects are seen.

By way of illustration, the compound described in Example 1 hereof had an $IC_{20}$ of about $10^{-5}$M in procedure (a) and had an $ED_{30}$ of about 4 mg/kg i.v. for reduction of heart rate in procedure (c). Other compounds of formula I exemplified hereinafter will in general show activity of the same general order.

As mentioned above the compounds of the present invention are of potential use in treating diseases/conditions of the cardiovascular system. Thus there is also provided a compound of the present invention for use in therapy, and the use of a compound of the present invention for the manufacture of a medicament for treating cardiovascular disease or conditions. In particular, the present invention also provides a method of modulating the action of the sino-atrial node in a warm-blooded mammal, such as man, requiring such treatment, which method comprises administering an effective amount of a compound of the present invention to said mammal.

In general, the pyrimidinium salts of formula I (or the related non-ionic anhydro-bases) will usually be administered in the form of a pharmaceutical composition, that is, together with a pharmaceutically acceptable diluent or carrier and such a composition is provided as a further feature of the invention. It will be recognised that it may be convenient to produce a particular pyridinium salt of formula I in situ, by using the appropriate anhydro-base and incorporating an acid of the formula HY during the production of a particular formulation.

A composition of the invention may be in a variety of dosage forms. For example, it may be in the form of tablets, capsules, solutions or suspensions for oral administration; in the form of a suppository for rectal administration; in the form of a sterile solution or suspension for administration by intravenous or intramuscular injection; in the form of an aerosol or a nebuliser solution or suspension, for administration by inhalation; in the form of a powder, together with pharmaceutically acceptable inert solid diluents such as lactose, for administration by insufflation; or in the form of a skin patch for transdermal administration. The compositions may conveniently be in unit dose form containing, for example, 5–200 mg of the compound of formula I.

A composition may be obtained by conventional procedures using pharmaceutically acceptable diluents and carriers well known in the art. Tablets and capsules for oral administration may conveniently be formed with a coating, such as an enteric coating (for example, one based on cellulose acetate phthalate) to minimise dissolution of the active ingredient of formula I in the stomach or to mask unpleasant taste.

The compositions of the invention may also contain one or more agents known to be of value in the diseases or conditions of the cardiovasculature intended to be treated. Thus, they may contain, in addition to the compound of formula I, for example, one or more other known agents selected from platelet aggregation inhibitors, prostanoid constrictor antagonists or synthase inhibitors (such as thromboxane $A_2$ antagonists or synthase inhibitors), cyclooxygenase inhibitors, hypolipidemic agents, anti-hypertensive agents (such as an angiotensin converting enzyme inhibitors, renin inhibitors or angiotensin antagonists), inotropic agents, β-adrenergic antagonists, thrombolytic agents, vasodilators and calcium channel antagonists.

In addition to their use in therapeutic medicine, the compounds of formula I are also useful as pharmacological tools in the development and standardisation of test systems for the evaluation of the new cardiovascular agents in laboratory animals such as cats, dogs, rabbits, monkeys, rats and mice.

The invention will now be illustrated by the following non-limiting Examples in which, unless otherwise stated:

(i) evaporations were carried out by rotary evaporation in vacuo;

(ii) operations were carried out at room temperature, that is in the range 18°–26° C.;

(iii) flash column chromatography or medium pressure liquid chromatography (MPLC) was performed on silica gel [either Fluka Kieselgel 60 (catalogue no. 60738) obtained from Fluka AG, Buchs, Switzerland, or Merck Kieselgel Art. 9385, obtained from E Merck, Darmstadt, Germany];

(iv) yields are given for illustration only and are not necessarily the maximum attainable by diligent process development;

(v) proton NMR spectra were normally determined at 200 MHz in deuterated dimethyl sulphoxide as solvent, using tetramethylsilane (TMS) as an internal standard, and are expressed as chemical shifts (delta values) in parts per million relative to TMS using conventional abbreviations for designation of major peaks: s, singlet; m, multiplet; t, triplet; br, broad; d,doublet; and (vi) all end-products were characterised by microanalysis, NMR and/or mass spectroscopy.

EXAMPLE 1

A mixture of 4-(1-indolyl)-6-methyl-2-methylaminopyridine (0.35 g, 1.48 mM), methyl iodide (0.5 ml) and dioxane (20 ml) was heated at 90° C. for 15 hours. The mixture was cooled. The solid was collected by filtration, washed with dioxan (10 ml) and then recrystallised from methanol. There was thus obtained 1,6-dimethyl-4-(1-indolyl)-2-methylaminopyridinium iodide (0.15 g, 27% yield), m.p. 275°–277° C.; microanalysis, found: C,49.3; H,4.7; N,10.3%; $C_{16}H_{18}N_3I$. $0.5H_2O$ requires: C,49.5; H,4.9; N,10.8%; NMR: 2.66(3H,s,$CH_3$), 3.1(3H,d, NH$CH_3$), 3.67(3H,s,$N^+CH_3$), 6.9(1H,d, indole-3H), 7.05 (1H,d,pyridine-3H), 7.2–7.4(3H, complex, pyridine 5-H and aromatic), 7.7(1H,d, aromatic), 7.9–8.0(2H, complex, aromatic and indole-2H), 8.15–8.25(1H,br,NH).

The pyridine starting material was prepared as follows:

(i) A mixture of 2,4-dichloro-6-methylpyridine (7.0 g) (West German Patent DE 2162238) and 33% w/v methylamine in ethanol (25 ml) was heated in a sealed tube at 100° C. for 8 hours. The solvent was removed by evaporation and the residual solid was purified by flash chromatography (Merck 9385 Silica, 100 g), using as eluant first an increasing gradient [20%–100% v/v] of diethyl ether in petrol (b.p. 60°–80° C.) and then an increasing gradient of up to 5% v/v methanol in dichloromethane. There was thus obtained 4-chloro-6-methyl-2-methylaminopyridine (0.8 g, 12% yield), m.p. 69°–70° C.; NMR: 2.2–2.3(3H,s, $CH_3$), 2.7–2.8 (3H,s,NH$CH_3$), 6.25(1H,s, pyridine-3H), 6.4(1H,s, pyridine-5H), 6.55–6.7(1H,br,NH).

(ii) A mixture of 4-chloro-6-methyl-2-methylaminopyridine (0.8 g, 5.1 mM), indoline (2.0 g) and N,N-dimethylformamide (DMF) (5 ml) was heated at 180° C. for 5 hours. The mixture was cooled and acetone (20 ml) was added. The grey solid (1.15 g) obtained was collected by filtration. A mixture of this solid (1.1 g) was heated with potassium hydroxide flake (0.26 g) in 2-propanol (30 ml) and water (3 ml) at 90° C. for 5 minutes. The mixture was cooled and the solvent removed by evaporation. Water (10 ml) was added. The precipitated solid was collected by filtration, washed with water, then with diethyl ether and air dried to give 4-(1-indolinyl)-6-methyl-2-methylaminopyridine as a solid (0.75 g, 61% yield), m.p. 174°–175° C.; NMR: 2.2(3H,s,$CH_3$), 2.7–2.8(3H, d,NH$CH_3$), 3.0–3.15(2H,t,$CH_2$), 3.85–3.95(2H,t,$CH_2$), 5.9(1H,d, pyridine-3H), 6.0–6.15 (1H,br,NH), 6.27 (1H,d, pyridine-5H), 6.7–6.85(1H,t, aromatic), 7.05–7.3(3H, complex, aromatic).

(iii) A mixture of 4-(1-indolinyl)-6-methyl-2-(methylamino)pyridine (0.45 g, 1.88 mM), 30% w/w palladium on charcoal (0.045 g) and diphenyl ether (10 ml) was heated under reflux for 45 minutes. The mixture was cooled. Diethyl ether (50 ml) was added and the catalyst removed by filtration through diatomaceous earth. The filter cake was washed with diethyl ether (50 ml). The filtrate and washings were concentrated under reduced pressure. The yellow solid obtained was further purified by flash chromatography (Merck 9385 silica, 100 g) eluting with diethyl ether to give 4-(1-indolyl)-6-methyl-2-methylaminopyridine as a solid (0.42 g, 90% yield), m.p. 156°–158° C.; NMR (CDCl$_3$): 2.45(3H,s,CH$_3$), 2.9–3.0(3H,d,NHC$\underline{H}_3$), 4.75–4.85(1H,br, NH), 6.3(1H,s, pyridine-3H), 6.6–6.7 (2H, complex, pyridine-5H and indole-3H), 7.15–7.4 (3H, complex, indole-2H and aromatic), 7.65–7.75(2H, complex, aromatic).

EXAMPLES 2–5

The procedure described in Example 1 was repeated using the appropriate substituted pyridine of the formula V (R$^5$=R$^7$=H; R$^6$=CH$_3$) and alkylating agent of formula R$^1$.Y. There were thus obtained the following compounds of formula I (R$^3$=R$^5$=H; R$^6$=CH$_3$; Y$^-$=I$^-$).

| Example | R$^1$ | R$^2$ | Q.N(R4)- | Recryst. Solvent | Melting Point (°C.) | Yield (%) |
|---|---|---|---|---|---|---|
| 2 | CH$_3$ | NHCH$_3$ | indolin-1-yl | ethanol | 274–275 | 20 |
| 3 | CH$_3$ | CH$_3$ | indol-1-yl | dioxan | 314–15 | 51 |
| 4 | CH$_3$ | CH$_3$ | N-ethyl-anilino | triturated + dioxan | 206–207 | 87 |
| 5 | Butyl | CH$_3$ | N-ethyl-anilino | ethyl acetate | 160–162 | 27 |

The starting material for Example 3 was prepared as described in a similar manner to Example 1. There was thus obtained 2,6-dimethyl-4-(1-indolyl)pyridine as a solid in 78% yield, m.p. 74°–75° C., by reaction of 2,6-dimethyl-4-(1-indolinyl)pyridine with 30% palladium on charcoal in diphenyl ether. 2,6-Dimethyl-4-(1-indolinyl)pyridine has been previously described (*Khim. Geterotsikl. Soedin*, 10, 1437).

The starting material for Examples 4 and 5, 2,6-dimethyl-4-(N-ethylanilino)pyridine, has been previously described (*J. Chem. Soc., Perkin I*, 973–978, 1983).

EXAMPLE 6

A mixture of 2,6-dimethyl-N-phenyl-4-chloropyridinium chloride (previously reported in *Annalen*, 1958, 617, 181–202) (2.19 g, 10 mM), N-ethylaniline (3.6 g, 30 mM) and ethanol (100 ml) was heated under reflux for 30 minutes. The solvent was removed by evaporation and the resultant syrup was purified by flash chromatography (Merck 9385 silica column, 180 g) using a 1:19 v/v mixture of methanol/methylene chloride as eluant. The resultant syrup was further purified by flash column chromatography using a neutral alumina column (ICN type N32-63, 150 g) and eluting with an increasing gradient (0–5% v/v) of methanol in dichloromethane. There was thus obtained 2,6-dimethyl-4-(N-ethylanilino)-N-phenylpyridinium chloride (1.9, 56% yield) as a pale orange glass; microanalysis, found: C,70.7; H,6.5; N,7.6; Cl,9.7%; C$_{21}$H$_{23}$N$_2$Cl.H$_2$O requires: C,70.7; H,7.0; N,7.85; Cl, 9.93%; NMR: 1.2–1.3(3H, t,CH$_2$C$\underline{H}_3$), 2.1(6H,5 pyridine-CH$_3$), 3.9–4.05(2H,q,C$\underline{H}_2$CH$_3$), 6.7–7.1(2H,br, pyridine-3H and -5H), 7.35–7.7 (10H, complex, aromatic).

EXAMPLE 7

A mixture of 1,6-dimethyl-4-(N-ethylanilino)-2-pyridone (0.15 g, 0.5 mM) and phosphorus oxychloride (2 ml) was heated under reflux for 1.5 hours. Excess phosphorus oxychloride was removed under vacuum by azeotropic distillation with toluene (2×3 ml toluene) to leave the chloride salt of the dichlorophosphinoyl derivative of the starting pyridone as the residue. A 33% w/v solution of methylamine in ethanol (10 ml) was then added to this material. After 3 hours, the solvent was evaporated from the resultant solution. The residue was dissolved in water (15 ml). The solution was acidified with 2M hydrochloric acid and extracted with methylene chloride (3×15 ml). The combined extracts were dried (MgSO$_4$) and the solvent evaporated. The residual gum was crystallised from acetone to give 1,6-dimethyl-4-(N-ethylanilino)-2-methylaminopyridinium chloride as a solid (0.066 g, 46% yield), m.p. 234°–235° C.; microanalysis, found C,65.6; H,7.6; N,14.1%; C$_{16}$H$_{22}$N$_3$Cl requires: C,65.9; H,7.6; N,14.4%; NMR: 1.1(3H,t, CH$_3$), 2.3(3H,s, C$\underline{H}_3$CH$_2$), 2.7(3H,d, NHC$\underline{H}_3$), 3.25(3H,s NCH$_3$), 3.8(2H,q, CH$_3$C$\underline{H}_2$), 5.5(1H,d, pyridine-H), 6.0(1H,d, pyridine-H), 7.2–7.6(6H, complex, phenyl-H+NH).

The pyridone starting material was obtained as follows:

(i) Trifluoromethanesulphonic anhydride (0.85 ml, 5 mM) was added dropwise to a stirred solution of 1,6-dimethyl-4-hydroxypyridin-2-one [0.7 g, 5 mM] (obtainable as described by Castillo et al., *Bull. Soc. Chim. France*, 1982, 257) in dry methylene chloride (15 ml). The resulting solution was kept at room temperature for 18 hours, washed with aqueous sodium carbonate solution, dried (MgSO$_4$) and the solvent evaporated. The residual solid was purified by flash chromatography (Merck 9385) using ether as eluant to give 1,6-dimethyl-4-(trifluoromethanesulphonyloxy)-2-pyridone as a solid (0.67 g), m.p. 65°–67° C.; NMR: 2.41(3H,s, CH$_3$) 3.53(3H,s, NCH$_3$), 6.05(1H,s, CH), 6.38(1H,s, CH).

(ii) A mixture of 1,6-dimethyl-4-(trifluoromethanesulphonyloxy)-2-pyridone (0.5 g, 1.8 mM) and N-ethylaniline (5 ml) was heated at an external temperature of 150° C. under argon for 24 hours. The solution was cooled. The precipitated material was purified by flash column chromatography (Merck 9385 silica) eluting first with ethyl acetate and then with ethyl acetate/ethanol (9:1 v/v). The 1,6-dimethyl-4-(N-ethylanilino)-2-pyridone product was characterised as the hydrochloride salt by addition of ethereal hydrogen chloride to a solution of the base in acetone. Addition of ether to the resultant solution gave 1,6-dimethyl-4-(N-ethylanilino)-2-pyridone hydrochloride as a solid (.0.255 g, 45% yield), m.p. 194° C. (softens at 180° C.); NMR: 1.15(3H,t, CH$_3$), 2.4(3H,s, CH$_3$), 3.48(3H,s, NC$\underline{H}_3$), 3.75(2H,q, CH$_2$), 6.02(1H, s, pyridine-H), 6.26(1H, s, pyridine-H), 7.25–7.6(5H, complex, phenyl-H), 7.6–8.6(3H and 1H, H$_2$O+HCl).

EXAMPLE 8

The procedure described in Example 7 was repeated using 1,6-dimethyl-4-(3-ethylindol-1-yl)-2-pyridone in place of 1,6-dimethyl-4-(N-ethylanilino)-2-pyridone. There was thus obtained 1,6-dimethyl-4-(3-ethylindol-1-yl)-2-methylaminopyridinium chloride as a solid (54% yield); m.p. 262° C. (with decomposition); microanalysis, found C, 65.3; H, 7.3; N, 12.8%; C$_{18}$H$_{22}$N3Cl. 0.75H$_2$O requires: C, 65.55; H, 7.15; N, 12.76%; NMR (CDCl$_3$): 1.35–1.45 (3H, t,CH$_2$C$\underline{H}_3$), 1.85–2.0 (broad, H$_2$O), 2.65(3H, s, CH$_3$), 2.75–2.9(2H, q, C$\underline{H}_2$—CH$_3$) 3.2(3H, s, NHC$\underline{H}_3$), 4.1(3H, s, +NM$\underline{e}$), 6.7(1H, s, pyridine C—$\underline{H}$), 6.85(1H, s, pyridine C—$\underline{H}$), 7.15(1H, s, indolyl 2-CH), 7.25–7.75(4H, complex, aromatic), 9.9–10.1(1H, broad, N$\underline{H}$).

The pyridone starting material was obtained as follows:

(i) A mixture of 1,6-dimethyl-4-(trifluoromethanesulphonyloxy)-2-pyridone (1.5 g, 5.5 mM) and 3-ethylindoline (1.22 g, 83 mM) was heated at an external temperature of 150° C. under argon for 3 hours. The solution was cooled. The residue was triturated with acetone to afford a solid which was collected by filtration. This solid was washed with acetone to give 1,6-dimethyl-4-(3-ethylindolin-1-yl)-2-pyridone as the hemi-trifluoromethylsulphonate salt; (1.76 g, 62% yield); m.p. 174°–175° C.; microanalysis, found C, 60.2; H, 6.0: N, 8.0%; $C_{18}H_{21}N_2 \cdot 0.5CF_3SO_3H$ requires: C, 60.1; H, 5.9; N, 8.0%: NMR $(DMSOd_6)$; 0.9–1.0(3H, t, $CH_2\underline{CH_3}$), 1.4–1.6(1H, m, C$\underline{H}$Et), 1.70–1.9(1H, m, C$\underline{H}$Et), 2.44(3H, s, $CH_3$), 3.25–3.4(1H, m, indoline H), 3.5(3H, s, +N$CH_3$), 3.6–3.7(1H, m, indoline H), 4.05–4.15(1H, m, indoline H), 6.2(1H, d, pyridine $\underline{CH}$), 6.6(1H, d, pyridine $\underline{CH}$), 6.9–7.05(1H, t, aromatic), 7.15–7.4(3H, m, aromatic).

(ii) This salt was dissolved in dichloromethane. The solution was washed with 2N Sodium Hydroxide solution (2×50 ml), water, dried over anhydrous magnesium sulphate, filtered and the solvent evaporated to give 1,6-dimethyl-4-(3-ethylindolin-1-yl)-2-pyridone as a solid (1.6 g). A mixture of this solid (1.6 g) and 30% w/w Palladium on charcoal (160 mg) was heated in diphenyl ether (10 ml) under reflux for two hours. The mixture was cooled, dichloromethane added and the catalyst removed by filtration through diatomaceous earth. The resultant filtrate was concentrated under reduced pressure. The residue was purified by flash column chromatography using silica (Merk 9385, 100 g), eluting with an increasing gradient (0–3% v/v) of methanol in dichloromethane. There was thus obtained 1,6-dimethyl-4-(3-ethylindol-1-yl)-2-pyridone as a pale orange syrup (1.2 g, 75% yield); NMR $(CDCl_3)$: 1.3–1.4(3H, t, $CH_2$—$\underline{CH_3}$), 2.35(3H, s, $CH_3$), 2.7–2.85(2H, q, $\underline{CH_2}$—$CH_3$), 3.6(3H, s, +N$CH_3$), 6.35(1H, d, pyridine-$\underline{CH}$), 6.6(1H, d, pyridine-$\underline{CH}$), 7.1(1H, s, indole $\underline{CH}$), 7.15–7.55(4H, complex, aromatic).

EXAMPLE 9

The procedure described in Example 7 was repeated using 1-ethyl-4(N-ethylanilino)-6-methyl-2-pyridone as starting material in place of 1,6-dimethyl-4-(N-ethylanilino)-2-pyridone. There was thus prepared 1-ethyl-4-(N-ethylanilino)-6-methyl-2-methylaminopyridinium chloride as a solid which was recrystallised from $Me_2CO/Et_2O$ as a hemihydrate (0.3 g, 49% yield); m.p. 155°–157° C.; microanalysis, found 64.6; H, 8.1; N, 12.9%; $C_{17}H_{24}N_3Cl \cdot 0.5H_2O$ requires: C, 64.9; H, 8.0; N, 13.3%; NMR: 1.1–1.3(6H, t, $2CH_3$), 2.42(3H, s, $CH_3$), 2.72–2.8 (3H, d, $\underline{CH_3}$NH), 3.75–3.9(2H, q, $CH_2$), 4.02–4.18(2H, q, $CH_2$), 7.22–7.6(5H, complex, aromatic), 7.75–7.9(1H, d, NH).

The pyridone starting material was obtained as follows.

To 4-anilino-6-methyl-2-pyridone (12.9 g, 64.5 mM) (Bisagni et al., J. Med. Chem., 26, 1329, 1983) in dry dimethylformamide (200 ml) was added portionwise a 60% suspension of sodium hydride in paraffin oil (6.45 g, 161 mM). After the addition was complete the mixture was stirred for a further 0.5 hours and then treated dropwise with ethyl iodide (11.6 ml, 142 mM). The mixture was stirred at room temperature for 18 hours and evaporated at reduced pressure. The residue was partitioned between water (100 ml) and methylene chloride (100 ml). The organic layer was separated, dried ($MgSO_4$) and evaporated to afford a gum which was purified by flash column chromatography (Merck 9385), eluting firstly with EtOAc as eluent to give 4-(N-ethylanilino)-2-ethoxy-6-methylpyridine, and then with 1:4 EtOH: EtOAc to give a gum. This gum was treated with ethereal hydrogen chloride to give a solid which was recrystallised from $Me_2CO/Et_2O$. There was thus obtained 1-ethyl-4(N-ethylanilino)-6-methyl-2-pyridone hydrochloride (4.2 g., 22% yield); m.p. 173°–174° C.; microanalysis, found C.65.0; H, 7.4; N, 9.4%; $C_{16}H_{21}N_2OCl$ requires C 65.6; H, 7.2; N, 9.6%; NMR $(CDCl_3)$ 1.1(6H, t, $2CH_3$), 2.4(3H, s, $CH_3$), 3.75(2H, q, $CH_2$), 6.01(2H, q, $CH_2$), 6.0(1H, s, CH), 6.3(1H, s, CH), 7.2–7.6(5H, complex, aromatic).

EXAMPLE 10

The procedure described in Example 7 was repeated using 4-(N-ethylanilino)-6-methyl-1-phenyl-2-pyridone as starting material in place of 1,6-dimethyl-4-(N-ethylanilino)-2-pyridone. There was thus prepared 4-(N-ethylanilino)-6-methyl-2-methylamino-1-phenylpyridinium chloride as a solid which was recrystallised from $Me_2CO/Et_2O$ as a hemidemihydrate (0.208 g, 43% yield); m.p. 173°–174° C.; microanalysis, found C, 70.6; H, 6.6; N, 11.4%; $C_{21}H_{24}N_3Cl \cdot 0.25H_2O$ requires: C, 70.4; H, 6.8; N, 11.7%; NMR $(CDCl_3)$: 1.18–1.25(3H, t, $CH_3$), 1.84(3H, s, $CH_3$), 2.62–2.64(3H, d, $CH_3$NH), 3.86–3.96(2H, q, $CH_2$), 5.63–5.64(1H,d, CH), 6.2(1H, d, CH), 6.24–6.27(1H, d, NH), 7.32–7.68(10H, complex, aromatic)

The pyridone starting material was obtained as follows:

(i) A 50% suspension of sodium hydride in paraffin oil (0.06 g, 1.2 mM) was washed with pentane and suspended in dry dimethylformamide (5 ml). 4-Anilino-6-methyl-1-phenyl-2-pyridone hydrochloride (0.276 g., 1 mM) [Kiang et al., J. Chem. Soc., C, 2721, 1971] was added and the mixture stirred for 0.25 hours. Ethyl iodide (0.4 ml, 5 mM) was added and the mixture stirred for 0.5 hours. The mixture was evaporated under reduced pressure and the residue partitioned between water (15 ml) and ethyl acetate (15 ml). The organic layer was dried ($MgSO_4$) and treated with ethereal hydrogen chloride to give a hydrochloride which was crystallised from isopropanol-ether to give 4-(N-ethylanilino)-6-methyl-1-phenyl-2-pyridone hydrochloride (0.16 g., 47% yield); m.p. 208°–210° C.; microanalysis, found C, 70.0; H, 6.3; N, 8.0%; $C_{20}H_{21}N_2OCl$ requires: C, 70.5; H, 6.2; N, 8.2%; NMR: 1.12–1.2(3H, t, $CH_3$), 1.94(3H, s, $CH_3$), 3.76–3.87(2H, q, $CH_2$), 5.98(1H, d, CH), 5.99(H, broad, NH+$H_2O$), 6.37(1H, d, CH), 7.31–7.61(10H, complex, aromatic).

EXAMPLE 11

A mixture of 4-(N-ethylanilino)-2-(2-hydroxyethylamino)-6-methylpyridine hydrochloride (0.8 g, 2.6 mM), thionyl chloride (1.0 ml, 13.8 mM) and methylene chloride (15 ml) was heated under reflux for 3 hours. The mixture was evaporated to dryness and the residue was purified by flash column chromatography, eluting with methanol: methylene chloride (1:9 v/v). The residue was dissolved in ethanol/water (1:1 v/v, 100 ml) and the solution passed down Amberlite* IRA400(OH) ion exchange resin (50 ml). The eluate (containing the product in its quaternary hydroxide form) was treated with dilute hydriodic acid to pH7 to give a solution of the quaternary iodide. This solution was evaporated to dryness to give a gum which was crystallised from acetone to give 2,3-dihydro-7-(N-ethylanilino)-5-methylimidazo[1,2-a]pyridinium iodide (0.27 g, 27% yield); m.p. 216°–217° C.; microanalysis, found C, 50.6; H, 5.5; N, 11.8%; $C_{16}H_{26}N_3I$ requires: C, 50.4; H, 5.2; N, 11.0%; NMR: 1.13–1.18(3H, t, $CH_3$), 2.33(3H, s, $CH_3$), 3.7–3.8(4H, m, $CH_2$—$CH_2$), 5.53(1H, s, CH), 6.14(1H, s, CH), 7.24–7.6(5H, complex, aromatic), 8.0(1H NH).

* Amberlite is a trade mark, the property of Rohm and Haas Co.

The pyridine starting material was obtained as follows.

(i) 4-(N-ethylanilino)-2-ethoxy-6-methylpyridine hydrochloride was prepared as described in Example 9, and was purified by flash chromatography. Elution with ethyl acetate gave a gum. This gum was treated with ethereal hydrogen chloride to give a solid which was recrystallised from acetone to give 4-(N-ethylanilino)-2-ethoxy-6-methylpyridine hydrochloride (8.1 g., 43% yield); m.p. 177°–178° C.; microanalysis, found C, 65.3; H, 7.4; N, 9.4%; $C_{16}H_{21}N_2OCl$ requires: C, 65.6; H, 7.2; N, 9.6%; NMR: 1.2(3H, t, $CH_3$), 1.4(3H, s, $CH_3$), 2.3(3H, s, $CH_3$), 3.9(2H, q, $CH_2$), 4.3(2H, q, $CH_2$), 6.0(1H, s, CH), 6.2(1H, s, CH), 7.3–7.65(5H, complex, aromatic).

(ii) 4-(N-ethylanilino)-2-ethoxy-6-methylpyridine hydrochloride (0.584 g, 2 mM) in ethanolamine (5 ml) was heated under argon at 180° C. for 24 hours. The solution was cooled, diluted with water (50 ml), basified with aqueous sodium carbonate solution and extracted with methylene chloride (4×10 ml). The organic extracts were combined, dried ($MgSO_4$) and evaporated to give a gum. This gum was triturated with ether to give, 4-(N-ethylanilino)-2-hydroxy-6-methylpyridine as a white solid (0.05 g) which was collected by filtration. The filtrate was evaporated and the residue was purified by flash column chromatography, eluting successively with methanol/methylene chloride (1:19 v/v), methanol/methylene chloride, (1:9 v/v/) and methanol/methylene chloride/0.88d aqueous $NH_4OH$ (20:80:1 v/v) to give a gum. This gum was dissolved in ethyl acetate and treated with etheral hydrogen chloride to give a gum which solidified on standing. The solid was washed with ether to give 4-(N-ethylanilino)-2-(2-hydroxyethylamino)-6-methylpyridine hydrochloride (0.15 g, 24% yield); m.p. 190° C.; microanalysis, found C, 62.2; H, 7.5; N, 13.7%; $C_{16}H_{22}N_3OCl$ requires: C, 62.4; H, 7.15; N, 13.6%; NMR: 1.1–1.2 (3H, t, $CH_3$), 2.23(3H, s, $CH_3$), 3.2–3.32(2H, q, $CH_2$), 3.5–3.6(2H, t, $CH_2$), 3.7–3.85(2H, q, $CH_2$), 5.7(1H, s, CH), 5.9(1H, s, CH), 7.2–7.6(5H, complex, aromatic), 4.7–5.1(1H, broad, OH), 12.4(1H, NH).

EXAMPLE 12

1,6-Dimethyl-4-(N-ethylanilino)-2-pyridone hydrochloride (see Example 7) (1 g 3.6 mM) was heated at 100° C. in phosphorus oxychloride (10 ml) for 3 hours. Excess phosphorus oxychloride was evaporated and a saturated solution of ammonia in ethanol (20 ml) was added to the residue obtained.

After standing at room temperature for 18 hours, the solution was evaporated. The residue was dissolved in water (20 ml), basified with aqueous sodium carbonate solution and extracted exhaustively with ether. The aqueous residue was evaporated to dryness and extracted with methylene chloride (5×10 ml). The combined organic extracts were dried ($MgSO_4$) and evaporated. The residual gum was purified by flash column chromatography. Elution with methanol/methylene chloride (1:19 v/v) gave a gum which was crystallised from acetone to give 1,6-dimethyl-2-ethoxy-4-(N-ethylanilino)pyridinium chloride demihemihydrate (0.09 g, 8% yield), m.p. 112°–114° C. (dec); microanalysis, found C, 65.6; H, 7.6; N, 9.3%; $C_{17}H_{23}N_2ClO$. $0.25H_2O$ requires: C, 65.6; H, 7.5; N, 9.0%; NMR: 1.1–1.2(3H, t, $CH_3$), 1.2–1.5(3H, t, $CH_3$), 2.45(3H, s, $CH_3$), 3.6(3H, s, $CH_3$), 3.85–4.0(2H, q, $CH_2$), 4.2–4.4(2H, q, $CH_2$), 6.13(1H, s, CH), 6.4(1H, s, CH), 7.2–7.6(5H, complex, aromatic).

EXAMPLES 13–15

The procedure described in Example 7 was repeated using the appropriate substituted pyridine of formula V ($R^3$=$R^5$=H, $R^6$=$CH_3$) and the intermediate chloride salt of the dichlorophosphinoyl derivative was treated with the appropriate amine in ethanol. There were thus obtained the following compounds of formula I ($R^3$=$R^5$=H, $R^6$=$CH_3$).

| Example | R1 | R2 | Q.N(R⁴)- | Y⁽⁻⁾ | Recryst Solvent | Melting Point (°C.) | Yield (%) |
|---|---|---|---|---|---|---|---|
| 13 | $CH_3$ | $NHCH_3$ | N-methyl-anilino | Cl | Acetone | 238–239 | 58 |
| 14 | $CH_3$ | $NHCH_3$ | N-butynyl-anilino | Cl | [a] | | 26 |
| 15 | $CH_3$ | $N(CH_3)_2$ | N-ethyl-anilino | I[b] | Acetone/ether | 173–174 | 35 |

[a] The product was isolated as a gum after flash chromatography on silica using methanol/dichloromethane 1:9 as eluent. NMR: 1.8(3H, s, C≡C—$CH_3$), 2.4(3H, s, $CH_3$), 2.8(3H, d, $NHCH_3$), 3.55(3H, s,⁺$NCH_3$), 4.5–4.7(2H, m, $CH_2$—C≡C—), 5.8(1H, s, pyridine-3H), 6.1(1H, s, pyridine-5H), 7.3–7.65(5H, br, aromatic), 7.75–7.9(1H, br, NH), Mass Spectrum: $M^+$ 280.

[b] The chloride product was obtained as a gum and was converted to the iodide as follows:

A solution of the reaction product in water (100 ml) was filtered through a small column of Amberlite* IRA-400 in the hydroxide form (approximate resin volume 20 ml). The fractions containing the product were combined and evaporated to small volume. A 5% aqueous solution of hydrogen iodide was added dropwise to pH7 and the solution was evaporated to dryness and the residue was crystallised.

The starting materials for examples 13 and 14 were prepared in a similar manner to the starting pyridone described in Example 7. There were thus obtained 1,6-dimethyl-4-(N-methylanilino)-2-pyridone, hydrochloride (37% yield), m.p. 201°–202° C. after recrystallisation from a mixture of acetone and ethyl acetate; and 1,6-dimethyl-4-(N-2-butynylanilino)-2-pyridone, hydrochloride as a gum (67% yield); NMR: 1.7(3H, s, C≡C—$CH_3$), 2.4(3H, s, $CH_3$), 3.5(3H, s, N—$CH_3$), 4.5(2H, d, $CH_2$—C≡C—), 6.0(1H, s, pyridine-3H), 6.24(1H, s, pyridine-5H), 7.2–7.6 (5H, m, aromatic). Mass Spectrum: $(M+H)^+ 267$.

* Amberlite is a trade mark, the property of Rohm and Haas Co.

EXAMPLE 16

The procedure described in Example 1 was repeated using 2-methyl-4-(N-ethylanilino)quinoline as starting material. There was thus obtained 1,2-dimethyl-4-(N-ethylanilino)quinolinium iodide (41% yield), m.p. 213°–215° C. (decomp) after crystallisation from a methanol/ether mixture. The starting quinoline was itself obtained by reaction of 4-chloro-2-methylquinoline with N-ethylaniline by the method described in example 1 and the 2-methyl-4-(N-ethylananilino)quinoline was obtained in 31% yield, m.p. 88°–90° C. after flash chromatography on silica.

EXAMPLE 17

The following illustrate representative pharmaceutical dosage forms containing a compound of formula I, such as is described in any of the preceding Examples or in the form of a salt with an alternative physiologically acceptable anion Y (hereafter referred to as "Compound X"), which may be used for therapeutic or prophylactic purpose in humans:

| (a) Tablet | mg/tablet |
|---|---|
| Compound X | 50 |
| Lactose Ph.Eur | 223.75 |
| Croscarmellose sodium | 6.0 |
| Maize starch | 15.0 |
| Polyvinylpyrrolidone (5% w/v paste) | 2.25 |
| Magnesium stearate | 3.0 |

| (b) Capsule | mg/capsule |
|---|---|
| Compound X | 10 |
| Lactose Ph.Eur | 488.5 |
| Magnesium stearate | 1.5 |

The above formulations may be obtained by conventional procedures well known in the pharmaceutical art. The tablets may be enteric coated by conventional means, for example to provide a coating of cellulose acetate phthalate.

We claim:

1. A compound of the formula I

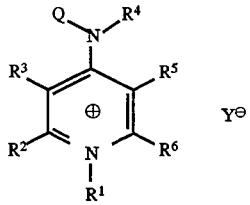

wherein $R^1$, $R^2$, $R^3$, $R^5$ and $R^6$ are selected from the following combinations:

(a) one of $R^2$ and $R^6$ is a basic group selected from amino, (1–6C)alkylamino, dialkylamino of up to eight carbon atoms, pyrrolidino, piperidino and morpholino, or is (1–6C)alkyl, (3–6C)alkenyl, (1–4C)alkoxy(1–4C)alkyl, (1–6C)alkoxy, (1–6C)alkylthio, phenyl, phenyl(1–4C)alkyl, (3–6C)cycloalkyl or (3–6C)cycloalkyl-(1–4C)alkyl; and the other of $R^2$ and $R^6$ is hydrogen, (1–6C)alkyl or one of the above defined basic groups; $R^1$ is (1–8C)alkyl, (3–6C)alkenyl, (4–7C)cycloalkyl, phenyl, phenyl(1–4C)alkyl, (3–6C)cycloalkyl-(1–4C)alkyl; and $R^3$ and $R^5$ are independently hydrogen, (1–4C)alkyl or (3–6C)alkenyl;

(b) $R^2$ is a basic group as defined above, $R^5$ and $R^6$ together form (3–6C)alkylene or, together with the appendant carbon atoms of the pyridine ring, complete a benzene ring; $R^1$ is as defined in (a) above; and $R^3$ is hydrogen, (1–4C)alkyl or (3–6C)alkenyl; and (c) $R^2$ is a basic group as defined above and $R^6$ is a group of the formula —$NR^7$.A— in which A together with $R^1$ forms an ethylene, trimethylene or tetramethylene link and $R^7$ is hydrogen or (1–6C)alkyl; and $R^3$ and $R^5$ have, independently, any of the meanings defined in (a) above; and wherein $R^4$ is hydrogen, (3–6C)cycloalkyl-(1–4C)alkyl, (1–6C)alkyl, (3–6C)alkenyl, (3–6C)alkynyl or phenyl(1–4C)alkyl; and Q is phenyl; or the group Q.N($R^4$)— together constitutes an azaheterocyclic moiety selected from pyrrolidine, pyrrole, piperidine, didehydropiperidine, morpholine, thiomorpholine and hexamethyleneimine, which azaheterocyclic moiety may itself optionally bear an (1–4C)alkyl, phenyl or phenyl(1–4C)alkyl substituent, or one or two benzene moieties fused thereto; Y is a physiologically acceptable anion; and any one or more of said phenyl or benzene moieties may optionally be unsubstituted or bear one or more substituents independently selected from halogeno, (1–4C)alkyl, (3–6C)alkenyl, (1–4C)alkoxy, cyano, trifluoromethyl, nitro, amino, hydroxy, (1–4C)alkylamino, dialkylamino of up to six carbon atoms, (1–4C)alkylthio, (1–4C)alkylsulphinyl, (1–4C)alkylsulphonyl and (1–4C)-alkylenedioxy.

2. A compound of the formula I as claimed in claim 1 wherein $R^1$, $R^2$, $R^3$, $R^5$ and $R^6$ are selected from the following combinations:

(a) one of $R^2$ and $R^6$ is a basic group selected from amino, methylamino, ethylamino, propylamino, butylamino, dimethylamino, diethylamino, methylpropylamino, dipropylamino, pyrrolidino, piperidino and morpholino, or is methyl, ethyl, isopropyl, butyl, allyl, but-2-enyl, 2-methyl-2-propenyl, methoxymethyl, 2-methoxyethyl, 2-ethoxyethyl, methoxy, ethoxy, propoxy, methylthio, ethylthio, phenyl, benzyl, 1-phenylethyl, 2-phenylethyl, cyclopropyl, cyclobutyl, cyclopentyl, cyclohexyl, cyclopropyl-methyl, cyclopentyl-methyl, cyclohexylmethyl, 2-(cyclohexyl)ethyl; and the other of $R^2$ and $R^6$ is hydrogen, methyl, ethyl, isopropyl, butyl, or one of the above defined basic groups; $R^1$ is methyl, ethyl, propyl, butyl, pentyl, allyl, but-2-enyl, 2-methyl-2-propenyl, methyl, ethyl, isopropyl, butyl, cyclopropyl, cyclobutyl, cyclopentyl, cyclohexyl, cycloheptyl, phenyl, benzyl, 1-phenylethyl, 2-phenylethyl, cyclopropyl-methyl, cylopentyl-methyl, cyclohexylmethyl, cyclohexylmethyl, 2-(cyclohexyl)ethyl; and $R^3$ and $R^5$ are independently hydrogen, methyl, ethyl, isopropyl, butyl, allyl, but-2-enyl or 2-methyl-2-propenyl;

(b) $R^2$ is a basic group as defined above, $R^5$ and $R^6$ together form a trimethylene, tetramethylene, pentamethylene or a group of the formula —$CH_2$.C($CH_3$)$_2$.$CH_2$— or —$CH_2$.C($CH_3$)$_2$.$CH_2$.$CH_2$—, or together with the appendant atoms of the pyridine ring complete a benzene ring; $R^1$ is as defined in (a) above; and $R^3$ is hydrogen, methyl, ethyl, isopropyl, butyl, allyl, but-2-enyl, 2-methyl-2-propenyl; and (c) $R^2$ is a basic group as defined above and $R^6$ is a group of the formula —NR7.A— in which A together with $R^1$ forms an ethylene, trimethylene or tetramethylene link and $R^7$ is hydrogen, methyl, ethyl, isopropyl or butyl; and $R^3$ and $R^5$ have, independently, any of the meanings defined in (a) above; and wherein $R^4$ is hydrogen, cyclopropyl-methyl, cylopentyl-methyl, cyclohexylmethyl, 2-(cyclohexyl)ethyl, methyl, ethyl, propyl, isopropyl, butyl, isobutyl, sec-butyl, pentyl, allyl, but-2-enyl, 2-methyl-2-propenyl, prop-2-ynyl, but-2-ynyl, benzyl, 1-phenylethyl or 2-phenylethyl; and Q is phenyl; or the group Q.N(R4)— together constitutes an azaheterocyclic moiety selected from pyrrolidine, pyrrole, piperidine, didehydropiperidine, morpholine, thiomorpholine and hexamethyleneimine, which azaheterocyclic moiety may itself optionally bear a methyl, ethyl, isopropyl, butyl, phenyl, benzyl, 1-phenylethyl or 2-phenylethyl substituent, or one or two benzene moieties fused thereto; Y is a physiologically acceptable anion; and any one or more of said phenyl or benzene moieties may optionally be unsubstituted or bear one or more substituents independently selected from cyano, trifluoromethyl, nitro, amino, hydroxy, fluoro, chloro, bromo, methyl, ethyl, propyl, allyl, 2-methyl-2-propenyl, methoxy, ethoxy, propoxy, methylamino, ethylamino, dimethylamino, diethylamino, methylthio, ethylthio, methylsulphinyl, ethylsulphinyl, methylsulphonyl, ethylsulphonyl, methylendioxy, and isopropylidenedioxy.

3. A compound as claimed in claim 2 wherein:
$R^4$ is methyl, ethyl, propyl, isopropyl, butyl, isobutyl, sec-butyl, pentyl, prop-2-ynyl, but-2-ynyl, benzyl, 1-phenylethyl, 2-phenylethyl, allyl, but-2-enyl, 2-methyl-2-propenyl, cyclopropylmethyl, cyclopentylmethyl, cyclohexylmethyl or 2-(cyclohexyl)ethyl, and Q is phenyl, 4-chlorophenyl, 4-methylphenyl, 2-nitrophenyl, 2-methoxyphenyl, 4-methylthiophenyl, 2,5-dinitrophenyl, 3,5-dimethylphenyl or 3,5-dichlorophenyl; or the group Q.N($R^4$)— constitutes an azaheterocyclic moiety selected from pyrrolidino, piperidino, morpholino, thiomorpholino, benzomopholino, 4-phenylpiperidino, hexamethyleneimino, 1,2,4,5-tetrahydro-1-pyridyl, 1,2,3,4-tetrahydro-1-quinolyl, 1,2,3,4-tetrahydro-2-isoquinolyl, 1-indolyl, 1-indolinyl, 3-methyl-1-indolinyl, 3-methyl-1-indolyl, 3-ethyl-1-indolyl, 3-ethyl-1-indolinyl, 3-propyl-1-indolyl, 5-bromo-1-indolyl, 9-carbazolyl, 10-phenothiazinyl and 10-phenoxazinyl.

4. A compound of the formula I wherein:

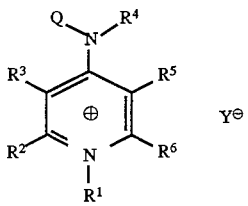

$R^1$ is (1-6C)alkyl, phenyl, phenyl(1-4C)alkyl or (3-6C) cycloalkyl; $R^2$ is hydrogen, (1-6C) alkyl, phenyl, phenyl (1-4C) alkyl, (3-6C) cycloalkyl or (3-6C) cycloalkyl-(1-4C) alkyl, amino, (1-4C)alkylamino or dialkylamino of up to 6 carbon atoms; $R^4$ is hydrogen, (3-6C)cycloalkyl-(1-4C)alkyl, (1-6C)alkyl, (3-6C) alkenyl, (3-6C)alkynyl or phenyl(1-4C)alkyl; and Q is phenyl;

or the group Q.N($R^4$)— together constitutes an azaheterocyclic moiety selected from pyrrolidine, pyrrole, piperidine, didehydropiperidine, morpholine and hexamethyleneimine, which azaheterocyclic moiety may itself optionally bear a methyl, ethyl, phenyl or benzyl substituent, or may have one or two benzene moieties fused thereto;

$R^5$ is hydrogen or methyl; $R^3$ is hydrogen; $R^6$ is a group of formula —NR$_e$R$_f$ in which Re and Rf are independently selected from hydrogen and (1–4C)alkyl, or together form (3–6C)alkylene; Y is a physiologically acceptable anion; and wherein any one or more of said phenyl or benzene moieties may optionally be unsubstituted or bear one or more substituents independently selected from halogeno, trifluoromethyl, cyano, nitro, (1–4C)alkyl and (1–4C)alkoxy.

5. A compound as claimed in claim 4 wherein: Q is phenyl; $R^1$ is methyl, ethyl, butyl, phenyl or cyclohexyl; $R^2$ is methyl, ethyl, amino, methylamino or ethylamino; $R^5$ is hydrogen; $R^3$ is hydrogen; $R^4$ is ethyl or $R^4$ is ethylene or vinylene completing an indoline or indole ring, respectively, including two adjacent carbon atoms of the benzene ring Q and the nitrogen atom of the group —N(R4)—; Re is hydrogen and Rf is methyl or ethyl; Y is a physiologically acceptable anion; and wherein the phenyl ring Q may optionally be unsubstituted or bear one or two substituents independently selected from fluoro, chloro, bromo, methyl, and methoxy.

6. A compound of the formula I wherein

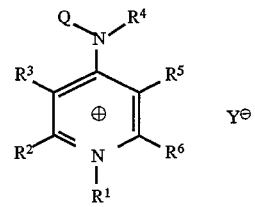

$R^1$ is (1–6C)alkyl, phenyl, phenyl(1–4C)alkyl or (3–6C) cycloalkyl;

$R^2$ is hydrogen, (1–6C)alkyl, phenyl, phenyl(1–4C)alkyl, (3–6C)cycloalkyl or (3–6C)cycloalkyl-(1–4C)alkyl, amino, (1–4C)alkylamino or dialkylamino of up to 6 carbon atoms;

$R^3$ is hydrogen;

$R^4$ is hydrogen, (3–6C)cycloalkyl-(1–4C)alkyl, (1–6C) alkyl, (3–6C)alkenyl, (3–6C)alkynyl or phenyl(1–4C) alkyl;

$R^5$ is hydrogen or methyl;
and Q is phenyl;

or the group Q.N($R^4$)— together constitutes an azaheterocyclic moiety selected from pyrrolidine, pyrrole, piperidine, didehydropiperidine, morpholine and hexamethyleneimine, which azaheterocyclic moiety may itself optionally bear a methyl, ethyl, phenyl or benzyl substituent or may have one or two benzene moieties fused thereto; $R^6$ is hydrogen or (1–4C)alkyl; Y is a physiologically acceptable anion; and wherein any one or more of said phenyl or benzene moieties may optionally be unsubstituted or bear one or more substituents independently selected from halogeno, trifluoromethyl, cyano, nitro, (1–4C) alkyl and (1–4C) alkoxy.

7. A compound as claimed in claim 6 wherein: Q is phenyl; $R^1$ is methyl, ethyl, butyl, phenyl or cyclohexyl; $R^2$ is methyl or ethyl; $R^5$ is hydrogen; $R^3$ is hydrogen; $R^4$ is ethyl or $R^4$ is ethylene or vinylene completing an indoline or indole ring, respectively, including two adjacent carbon atoms of the benzene ring Q and the nitrogen atom of the group —N($R^4$)—; $R^6$ is methyl or ethyl; Y is a physiologically acceptable anion; and wherein the phenyl ring Q may optionally be unsubstituted or bear one or two substituents independently selected from fluoro, chloro, bromo, methyl, and methoxy.

8. A compound of the formula I as claimed in claim 1 wherein the pyridinium ion is selected from:

1,6-dimethyl-4-(1-indolyl)-2-methylaminopyridinium;
4-(N-ethylanilino)-1,2,6-trimethylpyridinium;
2,6-dimethyl-4-(N-ethylanilino)-N-phenylpyridinium;
1,6-dimethyl-4-(N-ethylanilino)-2-methylaminopyridinium;
1,6-dimethyl-4-(3-ethylindol-1-yl)-2-methylaminopyridinium;
1-ethyl-4-(N-ethylanilino)-6-methyl-2-methylaminopyridinium;
4-(N-ethylanilino)-6-methyl-2-methylamino-1-phenylpyridinium;
1,6-dimethyl-4-(N-methylanilino)-2-methylaminopyridinium;
1,6-dimethyl-4-(N-butynylanilino)-2-methylaminopyridinium;
1,6-dimethyl-4-(N-ethylanilino)-2-dimethylaminopyridinium;
and Y is a physiologically acceptable counter-anion.

9. A compound as claimed in claim 1 in which Y is selected from halide, sulphate, fluoroborate, phosphate, nitrate, acetate, benzoate, butyrate, citrate, tartrate, dibenzoyltartrate, fumarate, trifluoroacetate, methosulphate and p-toluenesulphonate.

10. A non-ionic compound of formula Ia, Ib or Ic

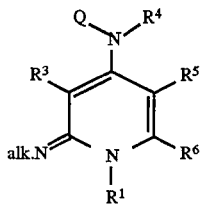

Ia

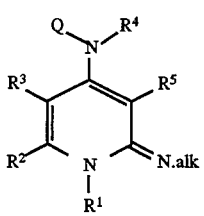

Ib

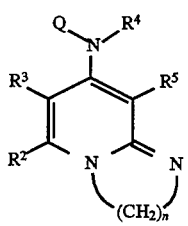

Ic (or a tautomeric form thereof when $R^4$ is hydrogen or when the other of the groups $R^2$ and $R^6$ is amino or alkylamino), wherein "alk" stands for (1–4C)alkyl; n is the integer 2,3 or 4; and wherein Q, $R^1$, $R^2$, $R^3$, $R^4$, $R^5$, and $R^6$ are as defined in claim 1.

11. A non-ionic compound of formula Ia, Ib or Ic

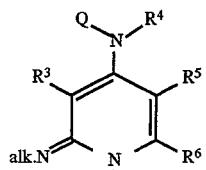

Ia

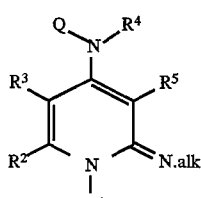

Ib

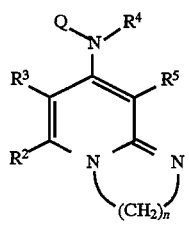

Ic (or a tautomeric form thereof when $R^4$ is hydrogen or when the other of the groups $R^2$ and $R^6$ is amino or alkylamino), wherein "alk" stands for (1–4C)alkyl; n is the integer 2,3 or 4; and Q, $R^1$, $R^2$, $R^3$, $R^4$, $R^5$, and $R^6$ are as defined in claim 4; or Q, $R^1$, $R^2$, $R^3$, $R^4$, $R^5$, and $R^6$ are as defined in claim 6.

12. A pharmaceutical composition comprising an active ingredient selected from a compound of formula I as claimed in claim 1, or a non-ionic compound having the formula Ia, Ib or Ic (or a tautomeric form thereof) as claimed in claim 10, together with or in admixture with a pharmaceutically acceptable diluent or carrier.

13. A method of modulating the action of the sino-atrial node in a warm-blooded animal requiring such treatment which comprises administering to said animal an effective amount of a pharmacologically active agent selected from the group consisting of a compound of the formula I as claimed in claim 1, or a non-ionic compound having the formula Ia, Ib or Ic (or a tautomeric form thereof) as claimed in claim 10.

* * * * *